US012588994B2

(12) United States Patent
Rafiee

(10) Patent No.: US 12,588,994 B2
(45) Date of Patent: Mar. 31, 2026

(54) DEVICES, SYSTEMS AND METHODS FOR REPAIRING LUMENAL SYSTEMS

(71) Applicant: Transmural Systems LLC, Andover, MA (US)

(72) Inventor: Nasser Rafiee, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 203 days.

(21) Appl. No.: 18/611,353

(22) Filed: Mar. 20, 2024

(65) Prior Publication Data

US 2024/0341955 A1      Oct. 17, 2024

Related U.S. Application Data

(63) Continuation of application No. 17/460,283, filed on Aug. 29, 2021, now abandoned, which is a continuation of application No. 16/557,171, filed on Aug. 30, 2019, now Pat. No. 11,357,627, which is a continuation of application No. 15/413,017, filed on
(Continued)

(51) Int. Cl.
| | |
|---|---|
| *A61F 2/24* | (2006.01) |
| *A61B 17/04* | (2006.01) |
| *A61B 17/064* | (2006.01) |
| *A61B 17/22* | (2006.01) |

(52) U.S. Cl.
CPC ........ *A61F 2/2436* (2013.01); *A61B 17/0401* (2013.01); *A61F 2/2409* (2013.01); *A61F 2/2418* (2013.01); *A61F 2/2454* (2013.01);

*A61F 2/2457* (2013.01); *A61B 2017/0409* (2013.01); *A61B 2017/0441* (2013.01); *A61B 2017/0649* (2013.01);
(Continued)

(58) Field of Classification Search
CPC ...... A61F 2/243; A61F 2/2409; A61F 2/2427; A61F 2/2436; A61F 2/2454; A61F 2/2418; A61F 2/2457; A61B 17/0401; A61B 17/12009
See application file for complete search history.

(56) References Cited

U.S. PATENT DOCUMENTS

| | | | |
|---|---|---|---|
| 4,106,129 A | 8/1978 | Carpentier et al. |
| 4,259,753 A | 4/1981 | Liotta et al. |
(Continued)

FOREIGN PATENT DOCUMENTS

| | | |
|---|---|---|
| EP | 2412397 A1 | 2/2012 |
| RU | 100 718 U1 | 12/2010 |
(Continued)

OTHER PUBLICATIONS

International Search Report, for related application No. PCT/US2011/059586, mailed May 25, 2012.
(Continued)

*Primary Examiner* — Tuan V Nguyen
(74) *Attorney, Agent, or Firm* — DeWitt LLP; Brian R. Pollack, Esq.

(57) ABSTRACT
The disclosure provides systems and related methods for delivering a prosthesis to a target location. The system includes a tether delivery catheter and a prosthesis delivery catheter, and also can include a lock delivery catheter or knot pusher, as desired. Various embodiments of useful valve prostheses are also disclosed.

12 Claims, 12 Drawing Sheets

Related U.S. Application Data

Jan. 23, 2017, now Pat. No. 10,398,551, which is a continuation-in-part of application No. 14/074,517, filed on Nov. 7, 2013, now Pat. No. 9,549,817.

(60) Provisional application No. 61/723,734, filed on Nov. 7, 2012.

(52) U.S. Cl.
CPC .............. *A61B 2017/22068* (2013.01); *A61F 2220/0008* (2013.01); *A61F 2250/0003* (2013.01)

(56) References Cited

U.S. PATENT DOCUMENTS

| | | | |
|---|---|---|---|
| 4,666,442 A | 5/1987 | Arru et al. | |
| 4,692,164 A | 9/1987 | Dzemeshkevich et al. | |
| 5,411,552 A | 5/1995 | Andersen et al. | |
| 5,449,384 A | 9/1995 | Johnson | |
| 5,606,928 A | 3/1997 | Religa et al. | |
| 5,788,715 A | 8/1998 | Watson, Jr. et al. | |
| 5,861,028 A | 1/1999 | Angell | |
| 5,895,410 A | 4/1999 | Forber et al. | |
| 5,928,281 A | 7/1999 | Huynh et al. | |
| 6,059,769 A | 5/2000 | Lunn et al. | |
| 6,106,510 A | 8/2000 | Lunn et al. | |
| 6,375,774 B1 | 4/2002 | Lunn et al. | |
| 6,599,303 B1 | 7/2003 | Peterson | |
| 6,602,271 B2 | 8/2003 | Adams et al. | |
| 6,716,231 B1 | 4/2004 | Rafiee et al. | |
| 6,733,525 B2 | 5/2004 | Yang et al. | |
| 6,790,229 B1 | 9/2004 | Berreklouw | |
| 6,797,000 B2 | 9/2004 | Simpson et al. | |
| 6,800,081 B2 | 10/2004 | Parodi | |
| 6,866,677 B2 | 3/2005 | Douk et al. | |
| 6,911,036 B2 | 6/2005 | Douk et al. | |
| 6,953,476 B1 | 10/2005 | Shalev | |
| 6,960,217 B2 | 11/2005 | Bolduc | |
| 7,044,958 B2 | 5/2006 | Douk et al. | |
| 7,066,946 B2 | 6/2006 | Douk et al. | |
| 7,189,259 B2 | 3/2007 | Simionescu et al. | |
| 7,195,641 B2 | 3/2007 | Palmaz et al. | |
| 7,201,772 B2 | 4/2007 | Schwammenthal et al. | |
| 7,294,135 B2 | 11/2007 | Stephens et al. | |
| 7,316,706 B2 | 1/2008 | Bloom et al. | |
| 7,399,315 B2 | 7/2008 | Iobbi | |
| 7,425,219 B2 | 9/2008 | Quadri | |
| 7,442,204 B2 | 10/2008 | Schwammenthal et al. | |
| 7,442,207 B2 | 10/2008 | Rafiee | |
| 7,445,631 B2 | 11/2008 | Salahieh et al. | |
| 7,481,838 B2 | 1/2009 | Carpentier et al. | |
| 7,491,232 B2 | 2/2009 | Bolduc et al. | |
| 7,524,330 B2 | 4/2009 | Berreklouw | |
| 7,655,040 B2 | 2/2010 | Douk et al. | |
| 7,682,352 B2 | 3/2010 | Rafiee et al. | |
| 7,699,892 B2 | 4/2010 | Rafiee et al. | |
| 7,716,801 B2 | 5/2010 | Douk et al. | |
| 7,753,840 B2 | 7/2010 | Simionescu et al. | |
| 7,753,949 B2 | 7/2010 | Lamphere et al. | |
| 7,780,726 B2 | 8/2010 | Seguin | |
| 7,799,069 B2 | 9/2010 | Bailey et al. | |
| 7,806,917 B2 | 10/2010 | Xiao | |
| 7,806,919 B2 | 10/2010 | Bloom et al. | |
| 7,815,673 B2 | 10/2010 | Bloom et al. | |
| 7,947,072 B2 | 5/2011 | Yang et al. | |
| 7,955,384 B2 | 6/2011 | Rafiee et al. | |
| 7,972,370 B2 | 7/2011 | Douk et al. | |
| 7,998,188 B2 | 8/2011 | Zilla et al. | |
| 8,002,825 B2 | 8/2011 | Letac et al. | |
| 8,052,750 B2 | 11/2011 | Tuval et al. | |
| 8,062,355 B2 | 11/2011 | Figulla et al. | |
| 8,070,802 B2 | 12/2011 | Lamphere et al. | |
| 8,092,518 B2 | 1/2012 | Schreck | |
| 8,092,520 B2 | 1/2012 | Quadri | |
| 8,092,524 B2 | 1/2012 | Nugent et al. | |
| 8,226,710 B2 | 7/2012 | Nguyen et al. | |
| 8,252,051 B2 | 8/2012 | Chau et al. | |
| 8,308,798 B2 | 11/2012 | Pintor et al. | |
| 8,337,541 B2 | 12/2012 | Quadri et al. | |
| 8,348,995 B2 | 1/2013 | Tuval et al. | |
| 8,348,996 B2 | 1/2013 | Tuval et al. | |
| 8,353,954 B2 | 1/2013 | Cai et al. | |
| 8,353,955 B2 | 1/2013 | Styrc et al. | |
| 2001/0021872 A1 | 9/2001 | Bailey et al. | |
| 2002/0032481 A1 | 3/2002 | Gabbay | |
| 2002/0138138 A1 | 9/2002 | Yang | |
| 2003/0055495 A1 | 3/2003 | Pease et al. | |
| 2003/0065386 A1 | 4/2003 | Weadock | |
| 2003/0097172 A1 | 5/2003 | Shalev et al. | |
| 2004/0087998 A1 | 5/2004 | Lee et al. | |
| 2004/0127916 A1 | 7/2004 | Bolduc et al. | |
| 2005/0038508 A1 | 2/2005 | Gabbay | |
| 2005/0043790 A1 | 2/2005 | Seguin | |
| 2005/0055082 A1 | 3/2005 | Ben-Muvhar et al. | |
| 2005/0137686 A1 | 6/2005 | Salahieh et al. | |
| 2005/0137769 A1 | 6/2005 | Salahieh et al. | |
| 2005/0143809 A1 | 6/2005 | Salahieh et al. | |
| 2005/0177180 A1 | 8/2005 | Kaganov et al. | |
| 2005/0288706 A1 | 12/2005 | Widomski et al. | |
| 2006/0085012 A1 | 4/2006 | Dolan | |
| 2006/0106449 A1 | 5/2006 | Ben-Muvhar | |
| 2006/0106450 A1 | 5/2006 | Ben-Muvhar | |
| 2006/0173537 A1 | 8/2006 | Yang et al. | |
| 2007/0043435 A1 | 2/2007 | Seguin et al. | |
| 2007/0067029 A1 | 3/2007 | Gabbay | |
| 2007/0118151 A1 | 5/2007 | Davidson | |
| 2007/0250160 A1 | 10/2007 | Rafiee | |
| 2007/0255398 A1 | 11/2007 | Yang et al. | |
| 2007/0288089 A1 | 12/2007 | Gurskis et al. | |
| 2007/0293942 A1 | 12/2007 | Mizraee | |
| 2008/0015687 A1 | 1/2008 | Lashinski et al. | |
| 2008/0021537 A1 | 1/2008 | Ben-Muvhar et al. | |
| 2008/0065191 A1 | 3/2008 | Bolduc et al. | |
| 2008/0077234 A1 | 3/2008 | Styrc | |
| 2008/0125860 A1 | 5/2008 | Webler et al. | |
| 2008/0208328 A1 | 8/2008 | Antocci et al. | |
| 2008/0221672 A1 | 9/2008 | Lamphere et al. | |
| 2009/0005863 A1 | 1/2009 | Goetz et al. | |
| 2009/0030434 A1 | 1/2009 | Paz | |
| 2009/0062841 A1 | 3/2009 | Amplatz et al. | |
| 2009/0069889 A1* | 3/2009 | Suri | A61F 2/2433 623/2.11 |
| 2009/0270966 A1 | 10/2009 | Douk et al. | |
| 2009/0270976 A1 | 10/2009 | Douk et al. | |
| 2009/0306768 A1 | 12/2009 | Quadri | |
| 2009/0319038 A1 | 12/2009 | Gurskis et al. | |
| 2010/0036479 A1 | 2/2010 | Hill et al. | |
| 2010/0082094 A1 | 4/2010 | Quadri et al. | |
| 2010/0100167 A1 | 4/2010 | Bortlein et al. | |
| 2010/0174363 A1 | 7/2010 | Castro | |
| 2010/0179648 A1 | 7/2010 | Richter et al. | |
| 2010/0179649 A1 | 7/2010 | Richter et al. | |
| 2010/0185275 A1 | 7/2010 | Richter et al. | |
| 2010/0191326 A1* | 7/2010 | Alkhatib | A61F 2/2439 623/2.11 |
| 2010/0249923 A1 | 9/2010 | Alkhatib et al. | |
| 2010/0262232 A1 | 10/2010 | Annest | |
| 2010/0280606 A1 | 11/2010 | Naor | |
| 2010/0298931 A1 | 11/2010 | Quadri et al. | |
| 2011/0106247 A1* | 5/2011 | Miller | A61F 2/2445 623/2.17 |
| 2011/0112632 A1 | 5/2011 | Chau et al. | |
| 2011/0137397 A1 | 6/2011 | Chau et al. | |
| 2011/0137409 A1 | 6/2011 | Yang et al. | |
| 2011/0172784 A1 | 7/2011 | Richter et al. | |
| 2011/0282438 A1 | 11/2011 | Drews et al. | |
| 2011/0313515 A1 | 12/2011 | Quadri et al. | |
| 2011/0319988 A1 | 12/2011 | Schankereli et al. | |
| 2011/0319989 A1 | 12/2011 | Lane et al. | |
| 2012/0022639 A1 | 1/2012 | Hacohen | |
| 2012/0059450 A1 | 3/2012 | Chiang et al. | |
| 2012/0078353 A1 | 3/2012 | Quadri et al. | |
| 2012/0078360 A1 | 3/2012 | Rafiee | |

(56) References Cited

U.S. PATENT DOCUMENTS

| | | |
|---|---|---|
| 2012/0179244 A1 | 7/2012 | Schankereli et al. |
| 2012/0215303 A1 | 8/2012 | Quadri et al. |
| 2012/0316642 A1 | 12/2012 | Yu et al. |
| 2012/0323316 A1 | 12/2012 | Chau et al. |
| 2013/0231701 A1 | 9/2013 | Voss |
| 2014/0018906 A1 | 1/2014 | Rafiee |
| 2014/0039083 A1 | 2/2014 | Krepski et al. |
| 2014/0094826 A1 | 4/2014 | Sutherland |
| 2014/0128965 A1 | 5/2014 | Rafiee |
| 2014/0163668 A1 | 6/2014 | Rafiee |
| 2014/0358223 A1 | 12/2014 | Rafiee et al. |
| 2015/0142021 A1 | 5/2015 | Smith |

FOREIGN PATENT DOCUMENTS

| | | |
|---|---|---|
| WO | WO2007121314 A2 | 10/2007 |
| WO | WO2012061809 A2 | 5/2012 |
| WO | WO2013131069 A1 | 9/2013 |
| WO | WO2015069947 A1 | 5/2015 |
| WO | WO2015148821 A1 | 10/2015 |

OTHER PUBLICATIONS

International Preliminary Report on Patentability and Written Opinion, or related application No. PCT/US2011/059586, mailed May 25, 2012.

BioIntegral Surgical, Mitral Valve Restoration System.

International Search Report for co-pending international application No. PCT/US2013/028774, mailed Jun. 14, 2013.

International Preliminary Report on Patentability and Written Opinion, on related application No. PCT/US2014/064431 mailed Mar. 26, 2015.

International Search Report, for related application No. PCT/US2015/022782, mailed Jun. 18, 2015.

* cited by examiner

Commissure screw / tether
anchor, P1 & P2 area, in place
and delivery removed

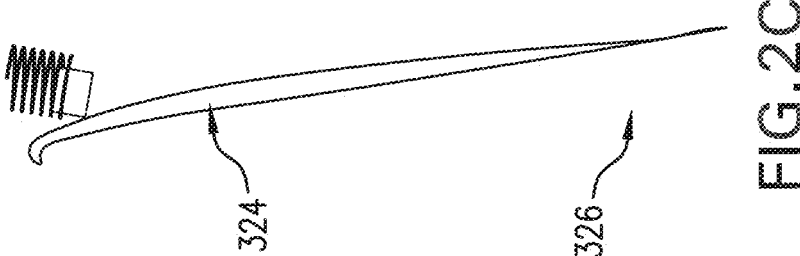
FIG.2C
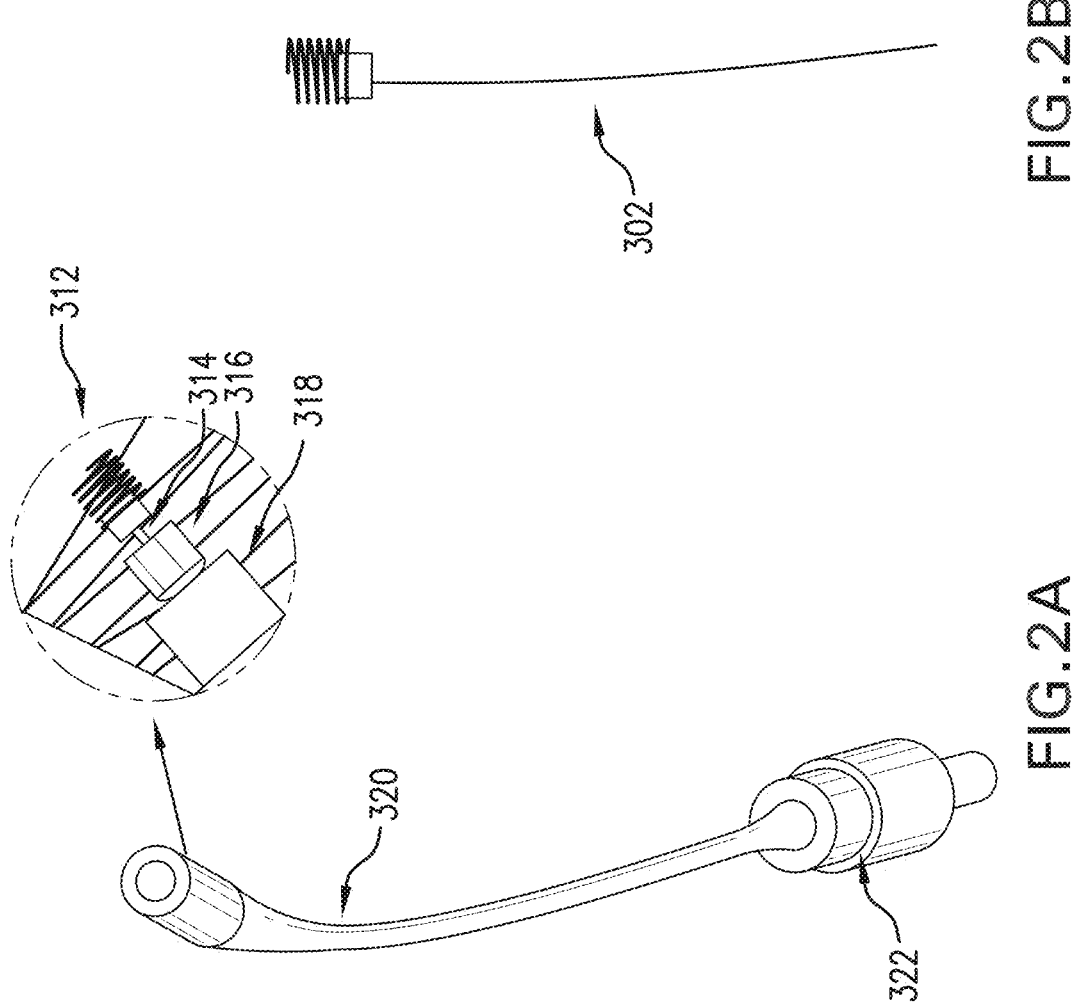
FIG.2B
FIG.2A

368

338

300

358

300

DEVICES, SYSTEMS AND METHODS FOR REPAIRING LUMENAL SYSTEMS

CROSS-REFERENCE TO RELATED APPLICATIONS

This patent application is a continuation of and claims the benefit of priority to U.S. patent application Ser. No. 17/460,283, filed Aug. 29, 2021, which in turn is a continuation of and claims the benefit of priority to U.S. patent application Ser. No. 16/557,171, filed Aug. 30, 2019 and issued as U.S. Pat. No. 11,357,627 on Jun. 14, 2022, which in turn is a continuation of and claims the benefit of priority to U.S. patent application Ser. No. 15/413,017, filed Jan. 23, 2017, now U.S. Pat. No. 10,398,551, which in turn is a continuation-in-part of, and claims the benefit of priority to, U.S. patent application Ser. No. 14/074,517, filed Nov. 7, 2013, now U.S. Pat. No. 9,549,817, issued Jan. 24, 2017, which in turn claims the benefit of priority to U.S. Provisional Patent Application Ser. No. 61/723,734, filed Nov. 7, 2012. This application is also related to U.S. patent application Ser. No. 13/240,793, filed Sep. 22, 2011, now abandoned, International Application No. PCT/US2013/28774, filed Mar. 2, 2013, and International Application No. PCT/US2011/59586, filed Nov. 7, 2011. The entire contents of each of the above referenced patent applications is incorporated herein by reference for any purpose whatsoever.

BACKGROUND

Heart valves permit unidirectional flow of blood through the cardiac chambers to permit the heart to function as a pump. Valvular stenosis is one form of valvular heart disease that prevents blood from flowing through a heart valve, ultimately causing clinically significant heart failure in humans. Another form of valvular disease results from heart valves becoming incompetent. Failure of adequate heart valve closure permits blood to leak through the valve in the opposite direction to normal flow. Such reversal of flow through incompetent heart valves can cause heart failure in humans.

The human mitral valve is a complicated structure affected by a number of pathological processes that ultimately result in valvular incompetence and heart failure in humans. Components of the mitral valve include the left ventricle, left atrium, anterior and posterior papillary muscles, mitral annulus, anterior mitral leaflet, posterior mitral leaflet and numerous chordae tendonae. The anterior leaflet occupies roughly ⅔ of the mitral valve area whereas the smaller posterior leaflet occupies ⅓ of the area. The anterior mitral leaflet, however, hangs from the anterior ⅓ of the perimeter of the mitral annulus whereas the posterior mitral leaflet occupies ⅔ of the annulus circumference. Furthermore, the posterior mitral leaflet is often anatomically composed of three separate segments. In diastole, the anterior leaflet and the three posterior leaflets are pushed into the left ventricle opening. In systole, the leaflets are pushed toward the plane of the mitral annulus where the posterior leaflets and larger anterior leaflet come into coaptation to prevent blood flow from the left ventricle to the left atrium. The leaflets are held in this closed position by the chordae tendonae. Dysfunction or failure of one or more of these mitral components may cause significant mitral valvular regurgitation and clinical disease in humans.

Surgical treatment has been the gold standard since its introduction in the 1950s. Currently, there are two surgical options offered for treatment. The first, mitral valve replacement, requires complex surgery using cardiopulmonary bypass to replace the mitral valve using a mechanical or bioprosthetic valvular prosthesis. Although a time-tested and proven strategy for treatment, bioprostheic valves suffer from poor long-term durability and mechanical valves require anticoagulation. As an alternative, surgical mitral valve repair has emerged as a superior procedure to achieve mitral valve competence and normal function. This operation is really a collection of surgical techniques and prostheses that collectively are referred to a mitral valve repair. Each component of the mitral valve can be altered, replaced, repositioned, resected or reinforced to achieve mitral valve competence.

Mitral annuloplasty has become a standard component of surgical mitral valve repair. In performing this procedure, the circumference of the mitral valve annulus is reduced and/or reshaped by sewing or fixing a prosthetic ring or partial ring to the native mitral valve annulus. As a consequence of mitral annuloplasty, the posterior mitral leaflet often becomes fixed in a closed position, pinned against the posterior left ventricular endocardium. The opening and closure of the mitral valve is subsequently based almost entirely on the opening and closing of the anterior mitral valve leaflet.

SUMMARY

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

To achieve these and other advantages and in accordance with the purpose of the disclosure, as embodied herein, in one aspect, the disclosure includes a tether delivery catheter for delivering an anchored tether to an anatomical location. The tether delivery catheter includes an elongate torqueable drive shaft having a proximal end that can have a first handle attached thereto and a distal end having a coupling for receiving an anchor. The tether delivery catheter further includes an anchor received in a torqueable relationship with the coupling of the distal end of the elongate torqueable drive shaft. The anchor has an anchoring portion to be advanced into an anatomical location, and at least one elongate tether extending proximally from the anchor toward the first handle. The tether delivery catheter further includes an outer tubular member having a proximal end, a distal end and an elongate body surrounding the elongate torqueable drive shaft. The outer tubular member can include a handle near or at its proximal end. The second handle is preferably rotatable with respect to the first handle about a central axis of the catheter to permit the anchor and elongate torqueable drive shaft to be rotated with respect to the outer tubular member.

If desired, the anchor can include a single tether, or a plurality of tethers, such as two tethers. When a plurality of tethers is provided, a loading needle can be provided that is disposed on a proximal end of the tethers to facilitate routing the tethers through the tether delivery catheter prior to use. The anchoring portion of the anchor can include a helical thread, for example, among other suitable retaining structures. The anchoring portion can be anchored into tissue by rotating the first handle with respect to the second handle while urging the anchor against the tissue. When a helical anchoring portion is provided, this relative rotation can effectuate implantation of the anchoring portion.

In further accordance with the disclosure, a prosthesis delivery catheter or system and a prosthesis are also provided. In an exemplary embodiment, this catheter/system can include an elongate inner body having a proximal portion and a distal tip. The distal tip includes a first proximally extending tubular member having a freely floating proximal end. The first proximally extending tubular member and elongate inner body cooperate to define a first substantially annular chamber. The catheter/system further includes an elongate tubular outer body having a proximal portion and a distal end. The elongate tubular outer body can be disposed about a proximal region of the elongate inner body.

The elongate tubular outer body can be axially displaceable with respect to the elongate inner body. The distal end of the elongate tubular outer body can be configured to substantially abut the proximal end of the first proximally extending tubular member. A distal region of the elongate tubular outer body and the proximal region of the elongate inner body can cooperate to define a second substantially annular chamber. The first and second chambers can cooperate to define a prosthesis chamber for receiving a compressed prosthesis.

The catheter/system can further be provided with a preloaded compressed prosthesis disposed about the elongate inner body in the prosthesis chamber. The compressed prosthesis can have at least one rail eyelet for receiving a flexible rail. The at least one rail eyelet can extend radially outwardly through a juncture defined between the distal end of the elongate tubular outer body and the proximal end of the first proximally extending tubular member. The compressed prosthesis can be configured to expand radially outwardly when the elongate inner body is advanced distally with respect to the elongate tubular outer body. The elongate inner body and tubular outer body can be withdrawn proximally through a lumen defined by the prosthesis after deployment of the prosthesis without needing to disturb the prosthesis or anything in physical contact with the prosthesis.

In some implementations, the catheter/system can further include a radiopaque marker mounted on the system proximate the prosthesis chamber, such as on the first proximally extending tubular member overlapping a central region of the prosthesis chamber. If desired, the compressed prosthesis can include a plurality of rail eyelets, wherein each rail eyelet is configured to receive a flexible rail. In some implementations, the compressed prosthesis can include two rail eyelets, wherein each rail eyelet is configured to receive a flexible rail.

In various implementations, the compressed prosthesis includes a generally tubular body adapted for placement proximate a mitral annulus. The tubular body can have a generally tubular upper portion adapted to substantially reside in the left atrium above the mitral annulus. The generally tubular upper portion can have a first circumferential wall that is outwardly biased to urge against cardiac tissue of the left atrium. The first circumferential wall can include a plurality of independently articulable frame portions configured to grip around the circumference of the atrial side of the mitral annulus. The prosthesis can also include a generally tubular lower portion extending downwardly from the generally tubular upper portion. The generally tubular lower portion is preferably configured to substantially reside in the left ventricle below the mitral annulus. The lower portion can be defined by an generally circumferential wall that extends downwardly from the generally tubular upper portion. The generally tubular lower portion can include at least one independently articulable anchor biased to extend radially outwardly from the generally tubular lower portion to urge against the ventricular side of the mitral annulus to prevent the prosthesis from moving through the mitral opening toward the atrium. The prosthesis can also include at least one prosthetic valve leaflet disposed within the tubular body, the at least one prosthetic valve leaflet being configured to occupy at least a portion of an opening defined by the generally tubular upper portion and the lower portion.

In some implementations, the prosthesis can include a plurality of independently articulable anchors biased to extend radially outwardly from the generally tubular lower portion to urge against the ventricular side of the mitral annulus to prevent the prosthesis from moving through the mitral opening toward the atrium. If desired, the prosthesis can include a fabric spanning across a framework of the prosthesis.

In other implementations, the compressed prosthesis can include a generally tubular body adapted for placement proximate a mitral annulus. The tubular body can have a generally tubular upper portion adapted to substantially reside in the left atrium above the mitral annulus. The generally tubular upper portion can have a first circumferential wall that is outwardly biased to urge against cardiac tissue of the left atrium. The first circumferential wall can include a plurality of independently articulable frame portions configured to grip around the circumference of the atrial side of the mitral annulus. The prosthesis can also include a generally tubular lower portion extending downwardly from the generally tubular upper portion. The generally tubular lower portion can be configured to substantially reside in the left ventricle below the mitral annulus. The lower portion can be defined by an generally circumferential wall that extends downwardly from the generally tubular upper portion. The generally tubular lower portion can include at least one downwardly extending pole for permitting attachment of a tissue valve. The prosthesis can similarly include at least one prosthetic valve leaflet disposed within the tubular body. The at least one prosthetic valve leaflet can be configured to occupy at least a portion of an opening defined by the generally tubular upper portion and the lower portion.

In further implementations, the compressed prosthesis can include a generally tubular body adapted for placement proximate a mitral annulus. The tubular body can have a generally tubular upper portion adapted to substantially reside in the left atrium above the mitral annulus. The generally tubular upper portion can have a first circumferential wall having a first circumferential end and a second circumferential end, and defining a first circumferential gap therebetween. The generally tubular upper portion can be biased to urge against cardiac tissue of the left atrium. The first circumferential wall can include a plurality of independently articulable frame portions configured to grip around the circumference of the atrial side of the mitral annulus. The prosthesis can further include a generally tubular lower portion extending downwardly from the generally tubular upper portion. The generally tubular lower portion can be configured to substantially reside in the left ventricle below the mitral annulus. The lower portion can be defined by a generally circumferential wall that extends downwardly from the generally tubular upper portion and has a first circumferential end and a second circumferential end separated by a second circumferential gap therebetween. The prosthesis can further include at least one prosthetic valve leaflet disposed within the tubular body, the at least one prosthetic valve leaflet being configured to occupy at least a portion of an opening defined by the generally tubular upper portion and the lower portion.

In further implementations, the prosthesis can include an inflatable bladder disposed in the generally tubular lower portion of the prosthesis. The inflatable bladder can being configured to be inflatable so as to facilitate adjustment of the prosthesis, such as during installation.

The disclosure further provides a lock deployment catheter having a proximal end and a distal end for delivering a deployable lock over a tether to an anatomical location. The catheter includes an outer tubular member having a proximal end, a distal end and an elongate tubular body defining a lumen therethrough, and an inner elongate member disposed in the lumen of the outer tubular member. The inner elongate member can include a proximal end, a distal end and an elongate body. The catheter can further include a deployable lock disposed in a distal region of the lumen of the outer tubular member. The deployable lock can be configured to be pushed distally out of the outer tubular member by displacing the inner elongate member distally with respect to the outer tubular member. The catheter can also include an elongate removable snare having a proximal end and a distal end with a hook configured to capture a filament. The snare can be routed along a path through the distal end of the lock deployment catheter, the lock and at least a portion of the outer tubular member. The snare can be configured to capture a filament and pull the filament along the path and out of a proximal portion of the catheter.

If desired, the lock deployment catheter can further include an axial compressive limit spring for biasing the inner elongate member in a proximal direction with respect to the outer tubular member. The inner elongate member can include a first handle disposed at the proximal end thereof and the outer tubular member can include a second handle disposed at the proximal end thereof. The limit spring can be compressed and the lock can be released when the handles are pushed together along a longitudinal axis of the catheter.

If desired, the lock deployment catheter can further include a lock housing disposed in the distal region of the outer tubular member. The lock housing can be configured to selectively receive the deployable lock. The lock can include a body with a first bore defined therein that is parallel to the lumen of the outer tubular member for receiving the snare therethrough, and a second bore oriented obliquely with respect to the first bore for receiving a spring loaded retainer. The spring loaded retainer can be in a first compressed state when the deployable lock is disposed in the outer tubular member. The spring loaded retainer can expand out of the second bore when the lock is urged distally outwardly of the catheter.

In some implementations, the lock can urge against the snare prior to pulling the filament through the catheter. If desired, the path can pass through an orifice formed in the spring loaded retainer.

The disclosure also provides systems and related methods for delivering a prosthesis to a target location. The system includes a tether delivery catheter as described herein and a prosthesis delivery catheter as described herein. The system can also include a lock delivery catheter or knot pusher, as desired.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 2(a) illustrates an exemplary articulating anchor and rail delivery system.

FIG. 2(b) illustrates an exemplary single rail tether and anchor.

FIG. 2(c) illustrates an exemplary double rail tether joined by a needle at a proximal end with an anchor, permitting the loading needle to be cut and the two ends of tethers for each anchor to be knotted and advanced to the surgical site to obviate the need for a lock.

DETAILED DESCRIPTION

Reference will now be made in detail to the present preferred embodiments of the disclosure, examples of which are illustrated in the accompanying drawings. The method and corresponding steps of the disclosed embodiments will be described in conjunction with the detailed description of the system.

Exemplary embodiments provide systems, devices and methods for repairing or replacing elements of the mitral valve, but it will be appreciated that similar approaches can be used to deliver other prostheses, such as lumenal stents, by providing the stent with at least one guide loop that extends outside of the delivery system so as to accept a guide rail. This can be particularly useful when delivering stents to lumenal locations that experience strong flow or pressure gradients and/or reversal in blood flow.

Exemplary elements of the valve prosthesis include the device frame, prosthetic posterior mitral leaflet equivalent and elements to prevent or reduce abnormal prolapse of the native anterior mitral leaflet during systole. Exemplary methods of implanting the valve prosthesis include direct open surgical placement, minimally invasive surgical placement either with or without the use of cardiopulmonary bypass, and totally catheter based implantation. Exemplary methods for maintaining the valve prosthesis in the preferred mitral annular location include external compression, compression following rail or suture guided implantation and seating with subsequent active or passive fixation of the valve prosthesis based upon the rail or suture guides.

Figure 1:
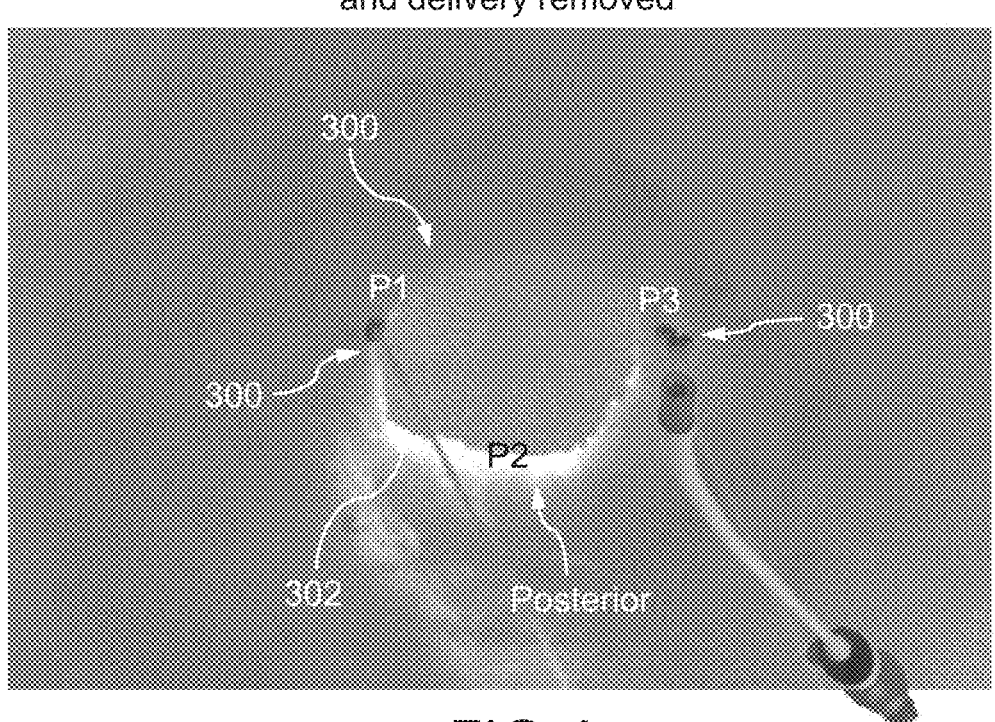
FIG. 1 illustrates an exemplary placement of an active rail fixation anchor/screw for both partial and full mitral valve replacement from a sub-annulus view of mitral valve region.
Figure 3C:
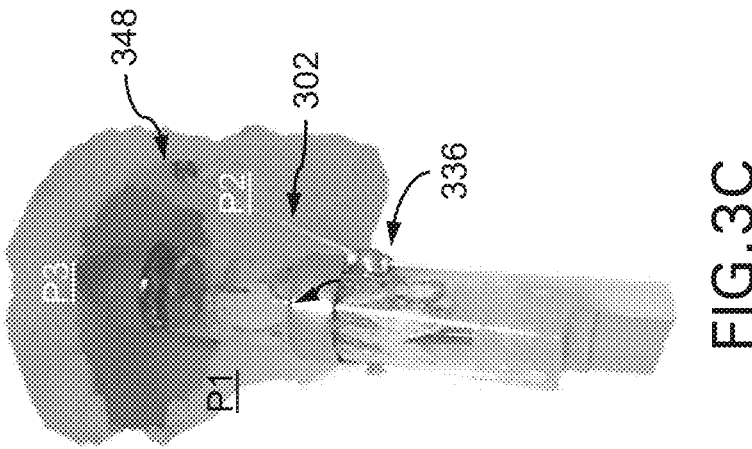
FIG. 3(c) illustrates advancement of an exemplary loaded prosthesis valve (full or partial replacement) delivery system over only rails anchored at location P2.
Figure 3B:
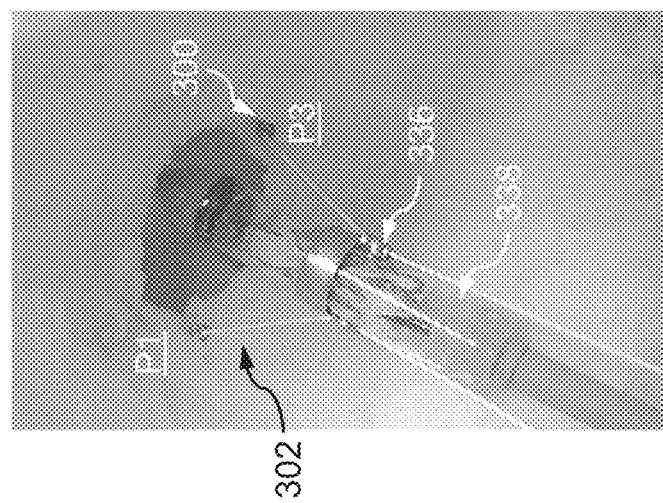
FIG. 3(b) illustrates a closer view of advancing an exemplary loaded prosthesis valve (full or partial replacement) delivery system over rails toward a mitral valve.
Figure 3A:
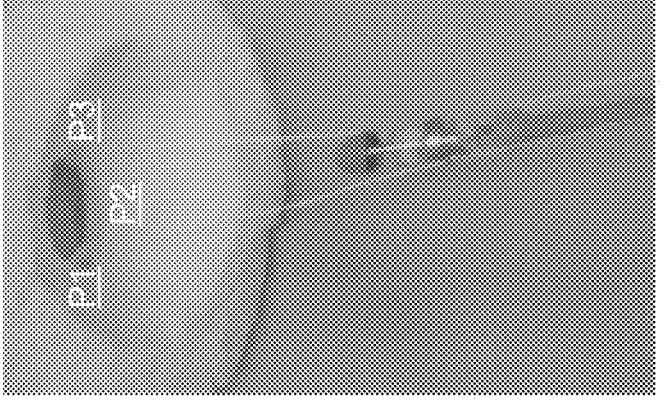
FIG. 3(a) illustrates advancing an exemplary loaded prosthesis valve (full or partial replacement) delivery system over a rail or tether to the mitral region.
Figure 3F:
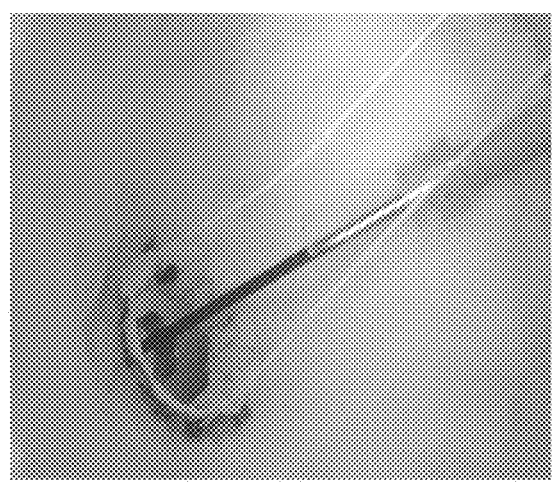
FIG. 3(f) illustrates an exemplary deployed full prosthesis over guide rails, wherein the prosthesis is in place, ready to be locked in place with locks.
Figure 3E:
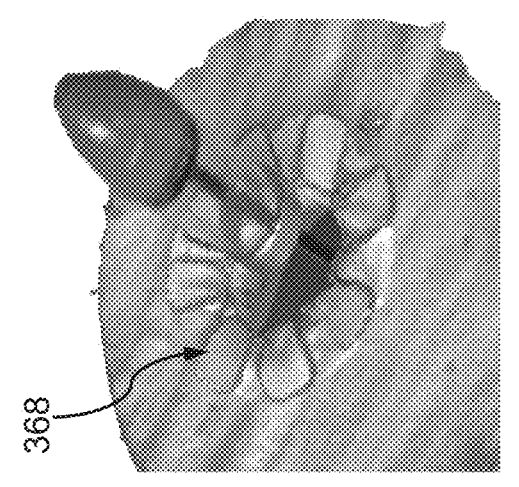
FIG. 3(e) illustrates deploying an exemplary prosthesis valve (full replacement) delivery system over active rails to the mitral valve.
Figure 3D:
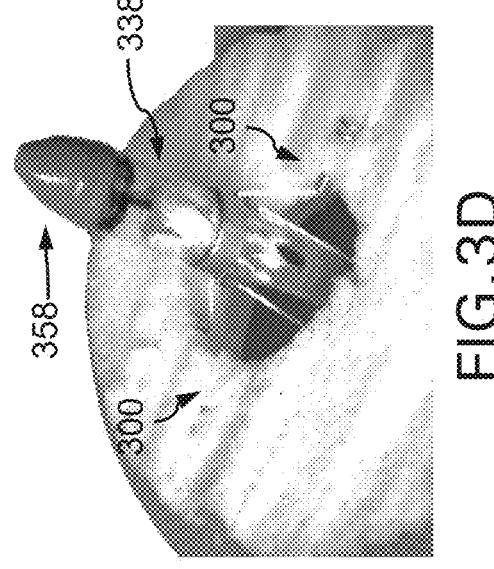
FIG. 3(d) illustrates advancing an exemplary loaded prosthesis valve (full or partial replacement) delivery system over rails to the mitral valve.
Figure 3I:
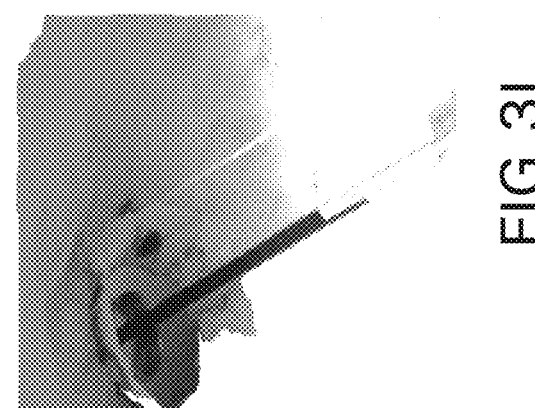
FIG. 3(i) illustrates an exemplary deployed partial prosthesis over guide rails, wherein the prosthesis is in place and ready to be secured.
Figure 3H:
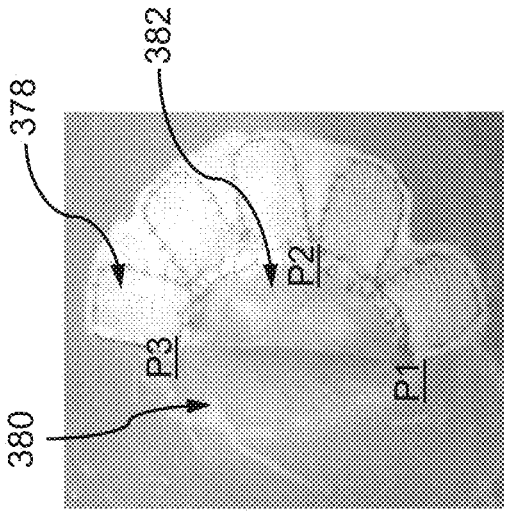
FIG. 3(h) illustrates an exemplary prosthesis with a tissue cover that coapts against a native anterior leaflet.
Figure 3G:
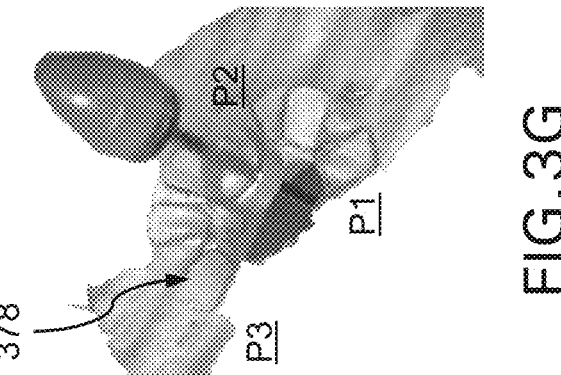
FIG. 3(g) illustrates deploying an exemplary prosthesis (partial replacement) delivery system over rails.

FIG. 1. illustrates placement of an active rail fixation anchor/screw for both partial and full mitral valve replacement from a sub-annulus view of mitral valve 300 region. Posterior sub-annulus and posterior leaflet fixation locations and numbers can vary depending on fixation requirements and prosthesis design. Should be from commissure to commissure along the posterior sub-annulus and posterior leaflet. Preferably P2 or P1 and P3.

Anchor Delivery Catheter

In accordance with a first aspect, the disclosure includes an anchor and tether delivery catheter for delivering an anchored tether to an anatomical location.

For purposes of illustration, and not limitation, as illustrated in FIGS. 2(*a*)-2(*c*), a tether delivery catheter 100 is provided that includes an elongate torqueable drive shaft 320 having a proximal end 102 that can have a first handle 322 attached thereto and a distal end 104 having a coupling or holding chamber 316 for receiving an anchor. The tether delivery catheter 100 further includes an anchor 312 received in a torqueable relationship with the coupling 316 of the distal end 104 of the elongate torqueable drive shaft 320. As shown in FIG. 2*a*, the anchor 312 has an anchoring portion to be advanced into an anatomical location, and at least one elongate tether 302 extending proximally from the anchor 312 toward the first handle 322. As shown in FIG. 2A, the tether delivery catheter 100 further includes an outer tubular member 318 having a proximal end, a distal end and an elongate body (not shown) surrounding the elongate torqueable drive shaft 320. The outer tubular member 318 can include a handle 106 near or at its proximal end, as illustrated. The second handle 106 is preferably rotatable with respect to the first handle about a central axis of the catheter to permit the anchor 312 and elongate torqueable drive shaft 320 to be rotated with respect to the outer tubular member 318.

If desired, the anchor 312 can include a single tether 302 as illustrated in FIG. 2(*a*), or a plurality of tethers 324, such as two tethers as illustrated in FIG. 2(*c*). When a plurality of tethers 324 is provided, a loading needle 326 can be provided that is disposed on a proximal end 328 of the tethers 302 to facilitate routing the tethers through the tether delivery catheter 100 prior to use. The anchoring portion of the anchor 312 can include a helical thread as illustrated, for example, among other suitable retaining structures. The anchoring portion can be anchored into tissue by rotating the first handle 322 with respect to the second handle 106 while urging the anchor 312 against the tissue. When a helical anchoring portion is provided, this relative rotation can effectuate implantation of the anchoring portion. This yields the arrangement in FIG. 1 wherein the anchors and tethers are attached to the mitral annulus 300. With these rails in place, a prosthesis can be threaded over the rail(s) and delivered to the mitral annulus. The tether(s) can include, in some implementations, a hollow braided suture material including a radiopaque core material inserted along its length such as a high density radiopaque fluoropolymer, radiopaque HDPE material, or other suitable radiopaque material.

Prosthesis Delivery Catheter

In further accordance with the disclosure as illustrated in FIGS. 3(*a*)-4(*c*), a prosthesis delivery catheter or system and a prosthesis are provided. As shown in FIGS. 3(*a*) and 4(*b*), in an exemplary embodiment, this catheter/system can include an elongate inner body 398 (FIG. 4*b*) having a proximal portion and a distal tip 358. The distal tip 358 includes a first proximally extending tubular member 393 having a freely floating proximal end. The first proximally extending tubular member 393 and elongate inner body 395 cooperate to define a first substantially annular chamber 392. The catheter/system further includes an elongate tubular outer body 320 having a proximal portion and a distal end. The elongate tubular outer body 320 can be disposed about a proximal region of the elongate inner body 395.

Figure 4C:
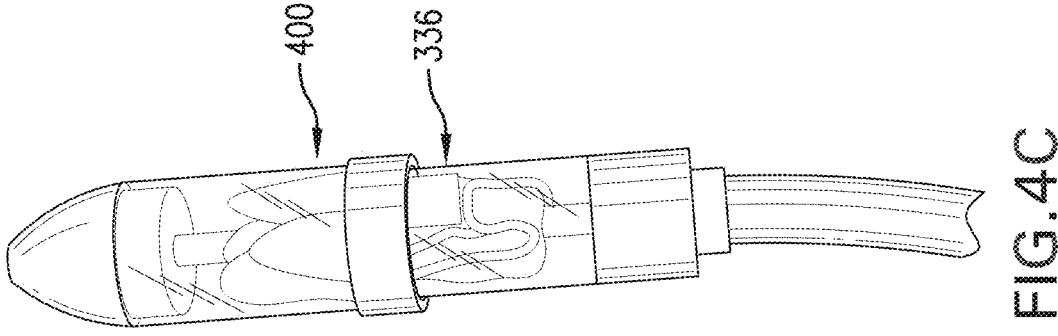
FIGS. 4(a), 4(b) and 4(c) illustrate different views of an exemplary prosthesis delivery system with a prosthesis.
Figure 4B:
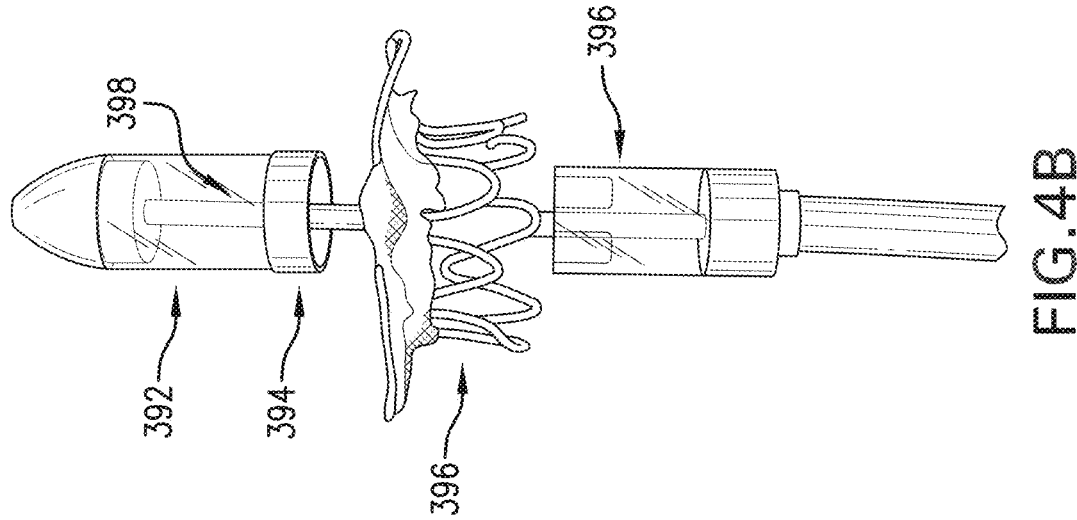
Figure 4A:
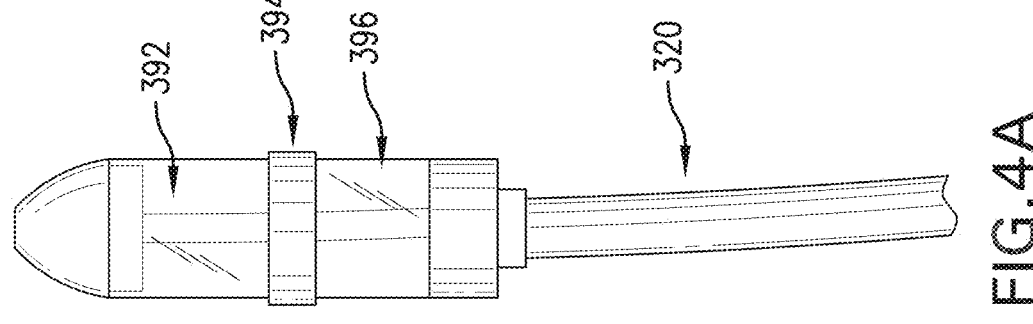

The elongate tubular outer body 320 can be axially displaceable with respect to the elongate inner body 395. The distal end of the elongate tubular outer body 320 can be configured to substantially abut the proximal end of the first proximally extending tubular member 393. A distal region of the elongate tubular outer body 320 and the proximal region of the elongate inner body 395 can cooperate to define a second substantially annular chamber 396. As shown in FIGS. 4(*a*) and 4(*b*) The first and second chambers 392, 396 can cooperate to define a prosthesis chamber 338 for receiving a compressed prosthesis 401.

As shown in FIG. 4(*c*), the catheter/system can further be provided with a preloaded compressed prosthesis 401 disposed about the elongate inner body 395 in the prosthesis chamber 338. The compressed prosthesis 401 can have at least one rail eyelet 336 for receiving a flexible rail. The at least one rail eyelet 336 can extend radially outwardly through a juncture defined between the distal end of the elongate tubular outer body and the proximal end of the first proximally extending tubular member. The compressed prosthesis 401 can be configured to expand radially outwardly when the elongate inner body 398 is advanced distally with respect to the elongate tubular outer body 320. The elongate inner body 398 and tubular outer body 320 can be withdrawn proximally through a lumen defined by the prosthesis after deployment of the prosthesis without needing to disturb the prosthesis or anything in physical contact with the prosthesis.

In some implementations, and as shown in FIG. 4(*a*) the catheter/system can further include a radiopaque marker 394 mounted on the system proximate the prosthesis chamber 338, such as on the first proximally extending tubular member 393 overlapping a central region of the prosthesis chamber 338. As shown in FIG. 4(*c*), if desired, the compressed prosthesis 401 can include a plurality of rail eyelets 336, wherein each rail eyelet 336 is configured to receive a flexible rail. In some implementations, the compressed prosthesis can include two rail eyelets 336, wherein each rail eyelet is configured to receive a flexible rail.

In various implementations as illustrated in the Figures, the compressed prosthesis 400 includes a generally tubular body 320 adapted for placement proximate a mitral annulus. As shown in FIG. 3(*e*), the tubular body 320 can have a generally tubular upper portion (e.g., 368) adapted to substantially reside in the left atrium above the mitral annulus 363. The generally tubular upper portion 368 can have a first circumferential wall 365 that is outwardly biased to urge against cardiac tissue 367 of the left atrium. The first circumferential wall 365 can include a plurality of independently articulable frame portions 369 configured to grip around the circumference of the atrial side of the mitral annulus 363. As shown in FIG. 3(*c*) and FIG. 3(*f*), the prosthesis can also include a generally tubular lower portion 371 extending downwardly from the generally tubular upper portion 368. The generally tubular lower portion 371 is preferably configured to substantially reside in the left ventricle below the mitral annulus 363. The tubular lower portion 371 can be defined by an generally circumferential wall that extends downwardly from the generally tubular upper portion 368. The generally tubular lower portion 371 can include at least one independently articulable anchor 348 biased to extend radially outwardly from the generally tubular lower portion 371 to urge against the ventricular side of the mitral annulus 363 to prevent the prosthesis from moving through the mitral opening toward the atrium. The prosthesis can also include at least one prosthetic valve leaflet disposed within the tubular body, the at least one prosthetic valve leaflet being configured to occupy at least a portion of an opening defined by the generally tubular upper portion and the lower portion.

Figure 8A:
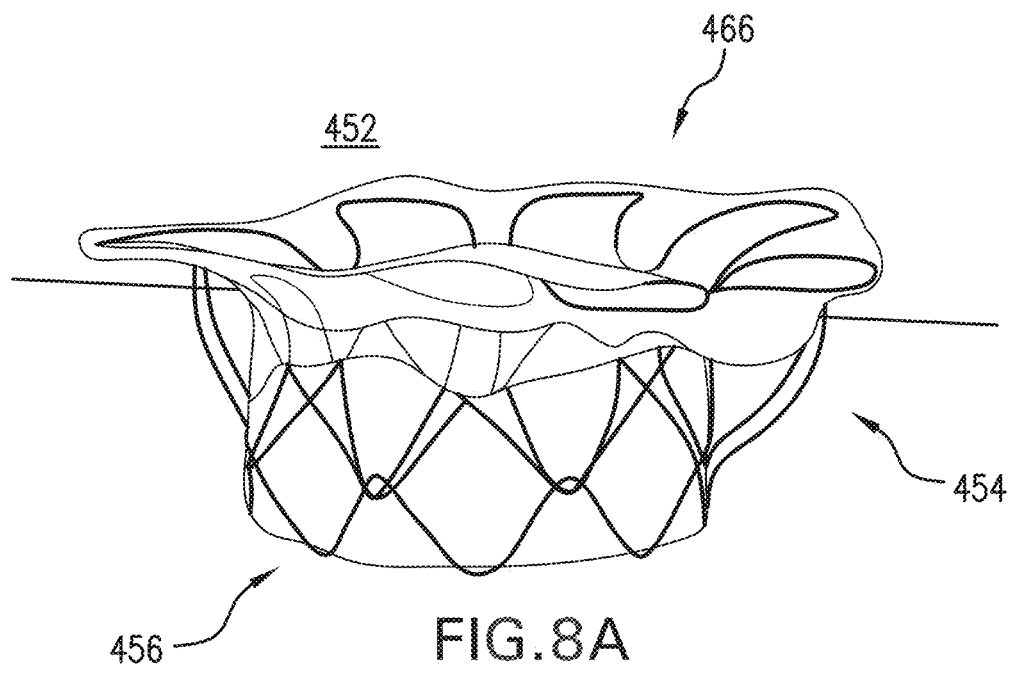
FIGS. 8(*a*) and 8(*b*) illustrate an exemplary full replacement prosthesis with self expanding anchors.
Figure 8B:
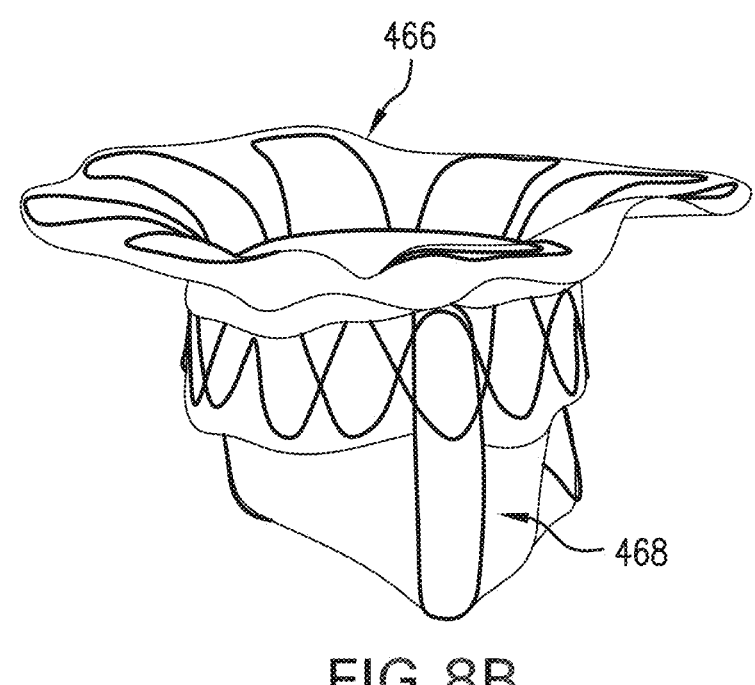

In some implementations (all illustrated embodiments and in FIG. 8(*a*)), the prosthesis can include a plurality of independently articulable anchors 454 biased to extend radially outwardly from the generally tubular lower portion to urge against the ventricular side of the mitral annulus to prevent the prosthesis from moving through the mitral opening toward the atrium. As shown in FIG. 3(*g*) and FIG. 3(*h*), if desired, the prosthesis can include a fabric 378 spanning across a framework of the prosthesis.

In other implementations (e.g., FIG. 8(*b*), 3(*c*), 3(*f*)), the compressed prosthesis 401 can include a generally tubular body adapted for placement proximate a mitral annulus. The tubular body can have a generally tubular upper portion adapted to substantially reside in the left atrium above the mitral annulus. The generally tubular upper portion can have a first circumferential wall that is outwardly biased to urge against cardiac tissue of the left atrium. The first circumferential wall can include a plurality of independently articulable frame portions configured to grip around the circumference of the atrial side of the mitral annulus. The prosthesis can also include a generally tubular lower portion extending downwardly from the generally tubular upper portion. The generally tubular lower portion can be configured to substantially reside in the left ventricle below the mitral annulus. The lower portion can be defined by an generally circumferential wall that extends downwardly from the generally tubular upper portion.

The generally tubular lower portion can include at least one downwardly extending pole 468 for permitting attachment of a tissue valve. The prosthesis can similarly include at least one prosthetic valve leaflet disposed within the tubular body. The at least one prosthetic valve leaflet can be configured to occupy at least a portion of an opening defined by the generally tubular upper portion and the lower portion.

Exemplary Prostheses

In further implementations (e.g., FIGS. 3(*g*)-3(*i*), 7(*b*). 7(*c*)), and as described above, the compressed prosthesis can include a generally tubular body adapted for placement proximate a mitral annulus. The tubular body can have a generally tubular upper portion adapted to substantially reside in the left atrium above the mitral annulus. The generally tubular upper portion can have a first circumferential wall having a first circumferential end and a second circumferential end, and defining a first circumferential gap therebetween. The generally tubular upper portion can be biased to urge against cardiac tissue of the left atrium. The first circumferential wall can include a plurality of independently articulable frame portions configured to grip around the circumference of the atrial side of the mitral annulus. The prosthesis can further include a generally tubular lower portion extending downwardly from the generally tubular upper portion. The generally tubular lower portion can be configured to substantially reside in the left ventricle below the mitral annulus. The lower portion can be defined by a generally circumferential wall that extends downwardly from the generally tubular upper portion and has a first circumferential end and a second circumferential end separated by a second circumferential gap therebetween. The prosthesis can further include at least one prosthetic valve leaflet 382 disposed within the tubular body, the at least one prosthetic valve leaflet being configured to occupy at least a portion of an opening defined by the generally tubular upper portion and the lower portion.

Figure 7A:
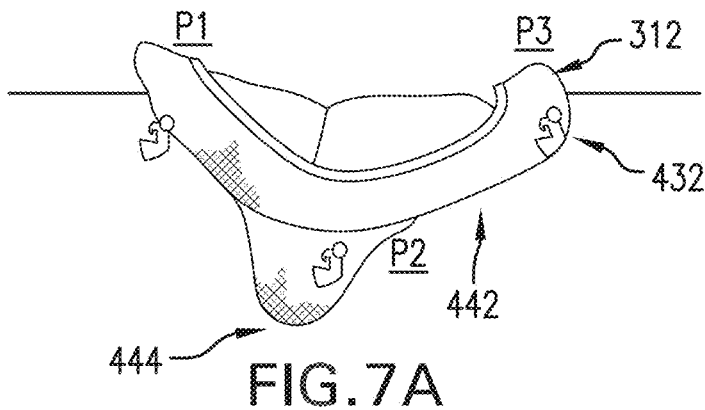
FIGS. 7(*a*), 7(*b*) and 7(*c*) illustrate an exemplary full retrievable partially compliant prosthesis with a tissue cover (partial replacement) delivered with guide rails anchored a locations P1, P2 and P3.
Figure 7B:
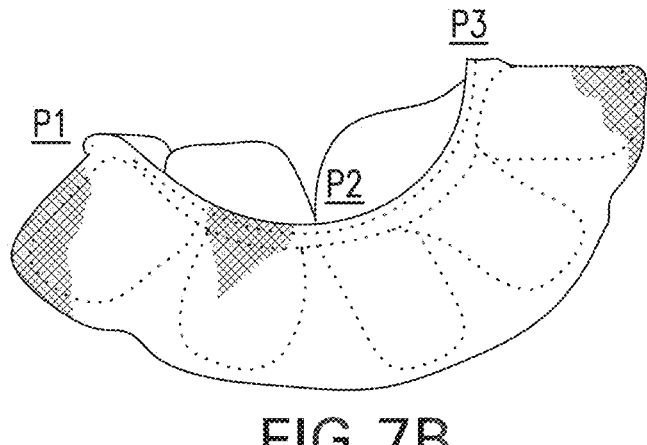
Figure 7C:
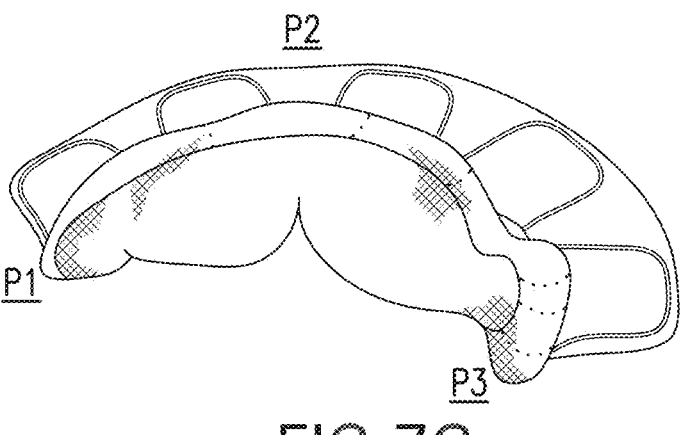

In further implementations (e.g., FIG. 7(*a*)), the prosthesis can include an inflatable bladder disposed in the generally tubular lower portion of the prosthesis. The inflatable bladder can being configured to be inflatable so as to facilitate adjustment of the prosthesis, such as during installation.

Lock Deployment Catheter

The disclosure further provides a lock deployment catheter (see FIGS. 5, 6) having a proximal end and a distal end for delivering a deployable lock 400 over a guide tether to an anatomical location. The catheter 500 (FIG. 5(*a*)) includes an outer tubular member 404 having a proximal end, a distal end and an elongate tubular body 405 defining a lumen therethrough, and an inner elongate member (not shown) disposed in the lumen of the outer tubular member 404. The inner elongate member can include a proximal end, a distal end and an elongate body. The catheter can further include a deployable lock 400 disposed in a distal region of the lumen of the outer tubular member 404. The deployable lock 400 can be configured to be pushed distally out of the outer tubular member 404 by displacing the inner elongate member distally with respect to the outer tubular member 404. In FIG. 6(*a*), the catheter 500 can also include an elongate removable snare 422 having a proximal end and a distal end with a hook configured to capture a filament. The snare 422 can be routed along a path through the distal end of the lock deployment catheter 500, the lock 400 and at least a portion of the outer tubular member 404. As illustrated in FIG. 6(*a*), the snare 422, and hence guide rail 402, can pass through the distal end of the lock catheter along a proximal direction and outside of the catheter though a hole in the outer wall of the catheter. The snare can 422 be configured to capture a filament and pull the filament along the path and out of a proximal portion of the catheter.

Figures 5A, 5B:
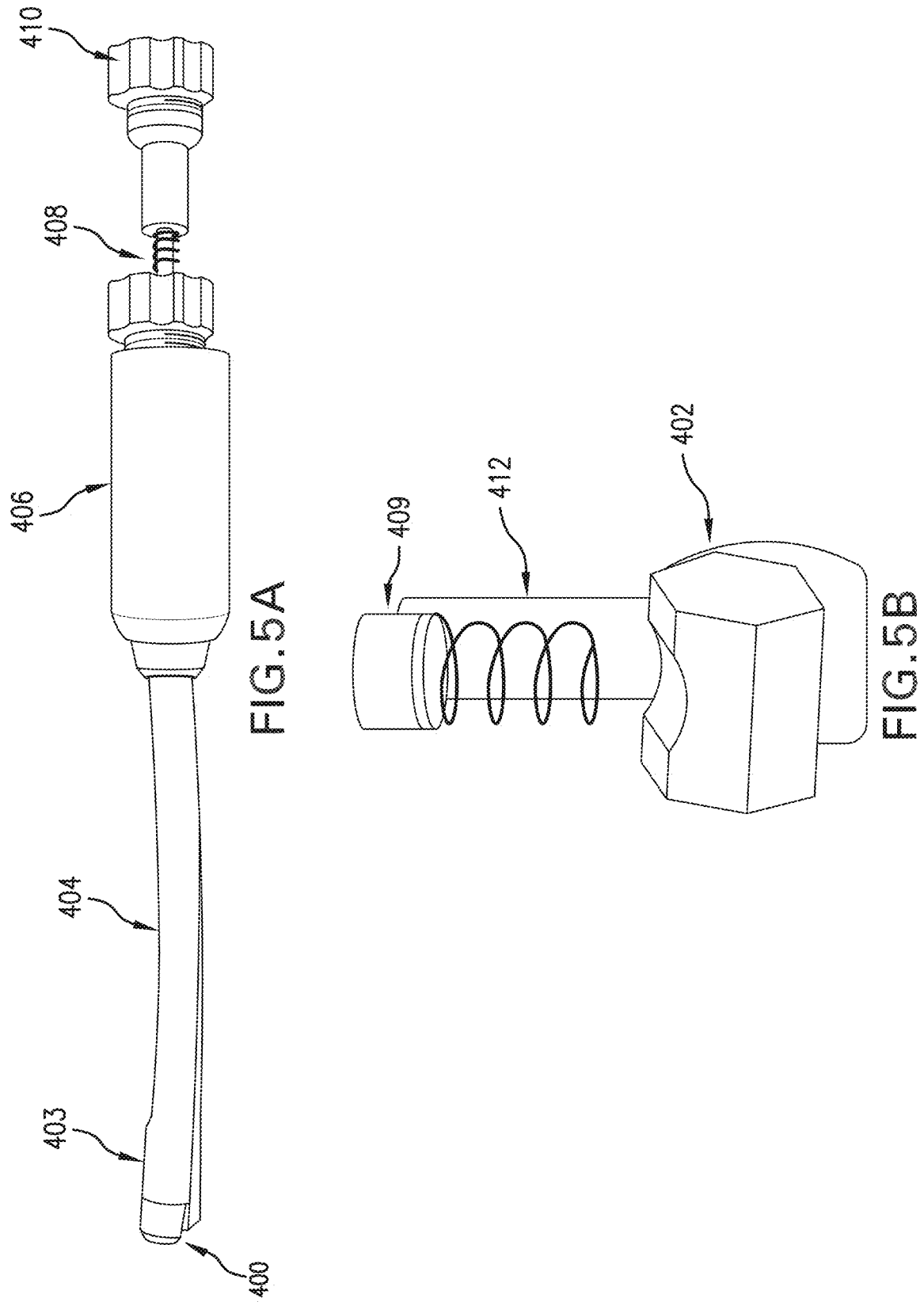
FIG. 5(a) illustrates an exemplary locking catheter.
FIG. 5(b) illustrates an exemplary lock for the locking catheter.
Figures 6A, 6B:
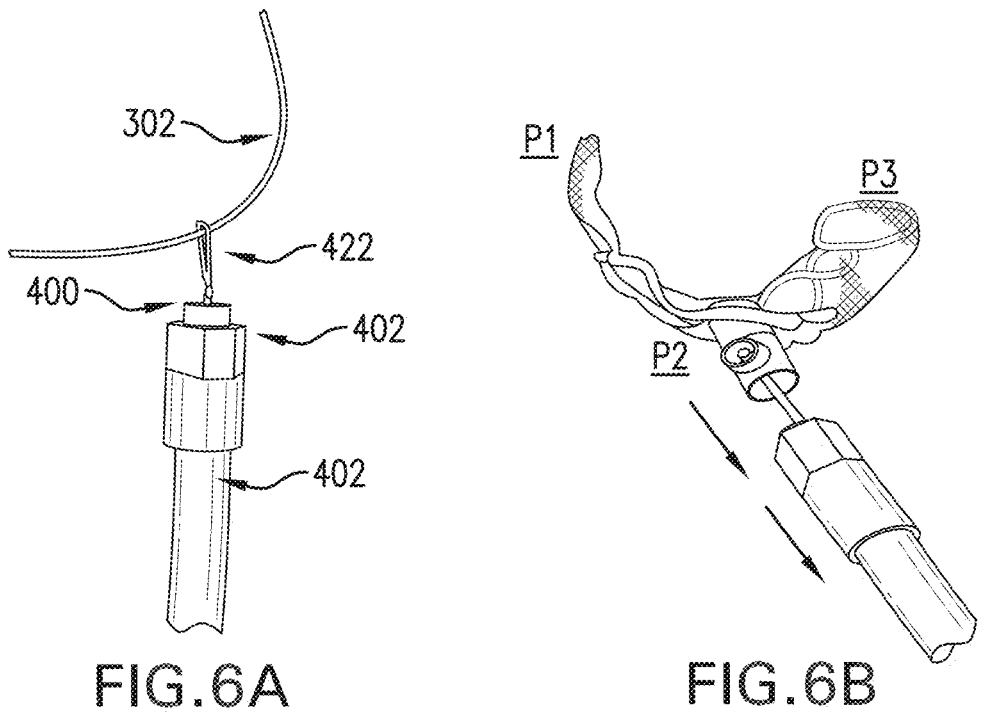
FIG. 6(a) illustrates an exemplary lock delivery system with lock and snare for threading a guide rail through the lock and delivery system.
FIG. 6(b) illustrates an exemplary lock released in place with the delivery catheter removed from a left ventricular ("LV") view.
Figure 6C:
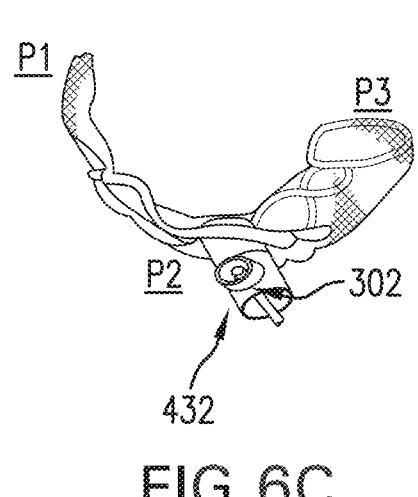
FIG. 6(c) illustrates an exemplary procedure completed using a partial mitral valve replacement prosthesis, LV view.
Figure 6D:
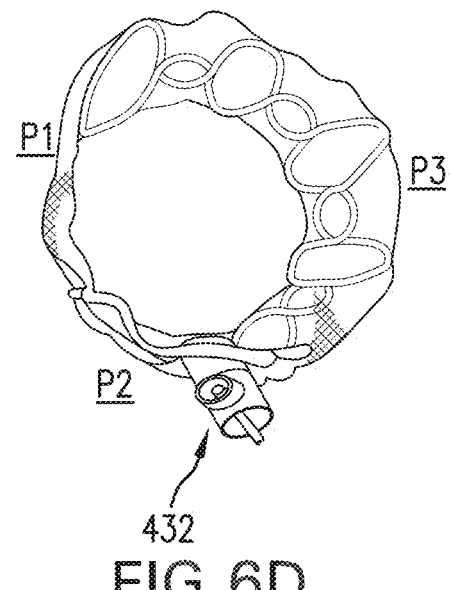
FIG. 6(d) illustrates an exemplary procedure using a full prosthesis, LV view.

As shown in FIG. 5(*a*), if desired, the lock deployment catheter 500 can further include an axial compressive limit spring 408 for biasing the inner elongate member in a proximal direction with respect to the outer tubular member 404. The inner elongate member can include a first handle 410 disposed at the proximal end thereof and the outer tubular member can include a second handle 406 disposed at the proximal end thereof. The limit spring can be compressed and the lock can be released when the handles are pushed together along a longitudinal axis of the catheter.

If desired, the lock deployment catheter can further include a lock housing 403 disposed in the distal region of the outer tubular member. The lock housing 403 can be configured to selectively receive the deployable lock 400. As illustrated in FIG. 5(*b*), the lock 400 can include a body 402 with a first bore defined therein that is parallel to the lumen of the outer tubular member 404 for receiving the snare 422 therethrough, and a second bore oriented obliquely with respect to the first bore for receiving a spring loaded retainer 412. The spring loaded retainer 412 can be in a first compressed state when the deployable lock 400 is disposed in the outer tubular member 404. The spring loaded retainer 412 can expand out of the second bore when the lock is urged distally outwardly of the catheter.

In some implementations, the lock can urge against the snare prior to pulling the filament through the catheter. If desired, the path can pass through an orifice 409 formed in the spring loaded retainer.

Systems, Kits and Delivery Methods

The disclosure also provides systems and related methods for delivering a prosthesis to a target location. The system includes a tether delivery catheter as described herein and a prosthesis delivery catheter as described herein. The system can also include a lock delivery catheter or knot pusher, as desired.

Figure 9:
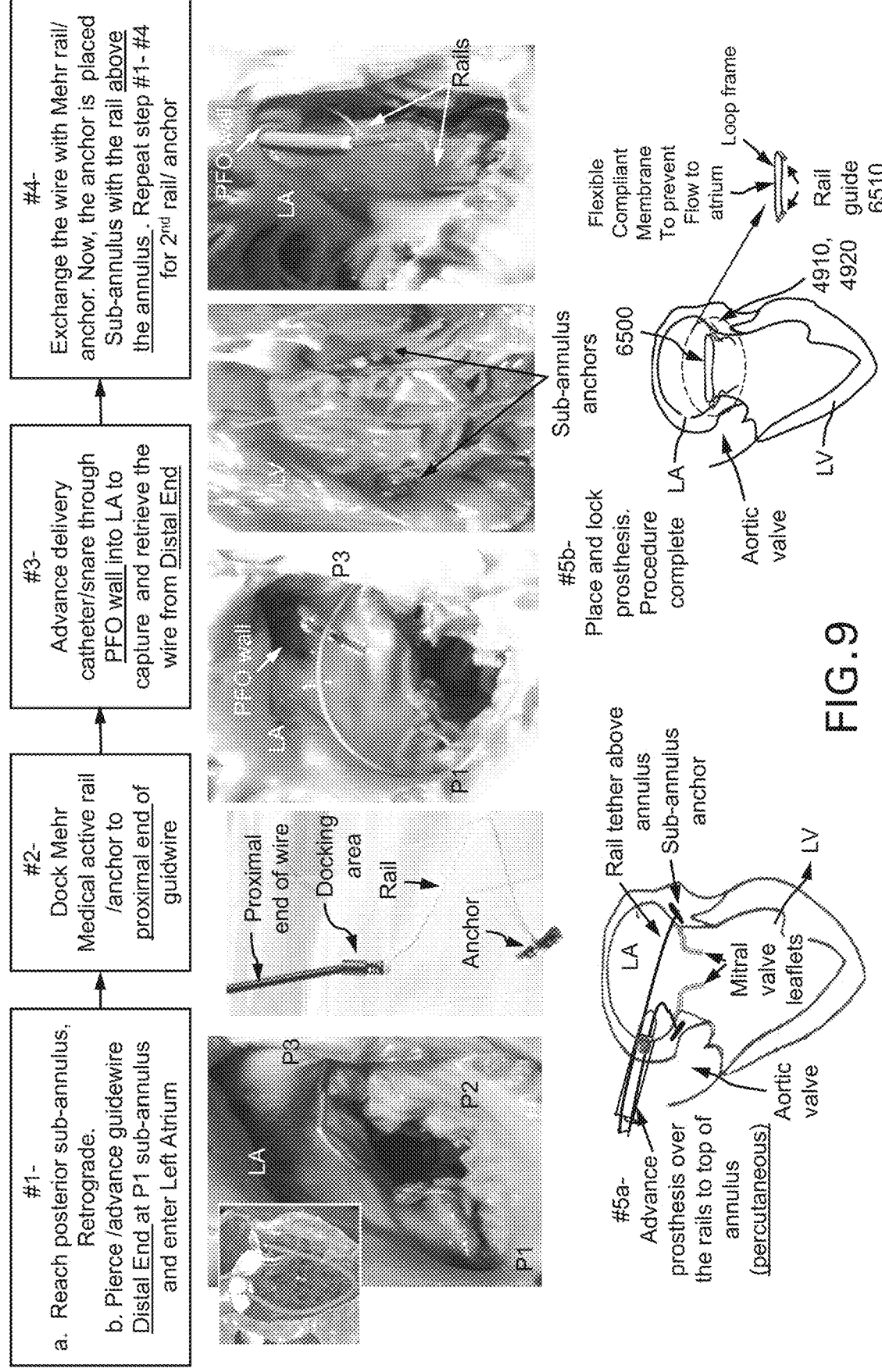
FIG. 9 illustrates an exemplary guide rail based prosthesis delivery technique using a percutaneous approach that permits delivery and fixation of a prosthesis to the top of mitral annulus while preserving the native leaflets and sub-annulus anatomy.
Figure 10:
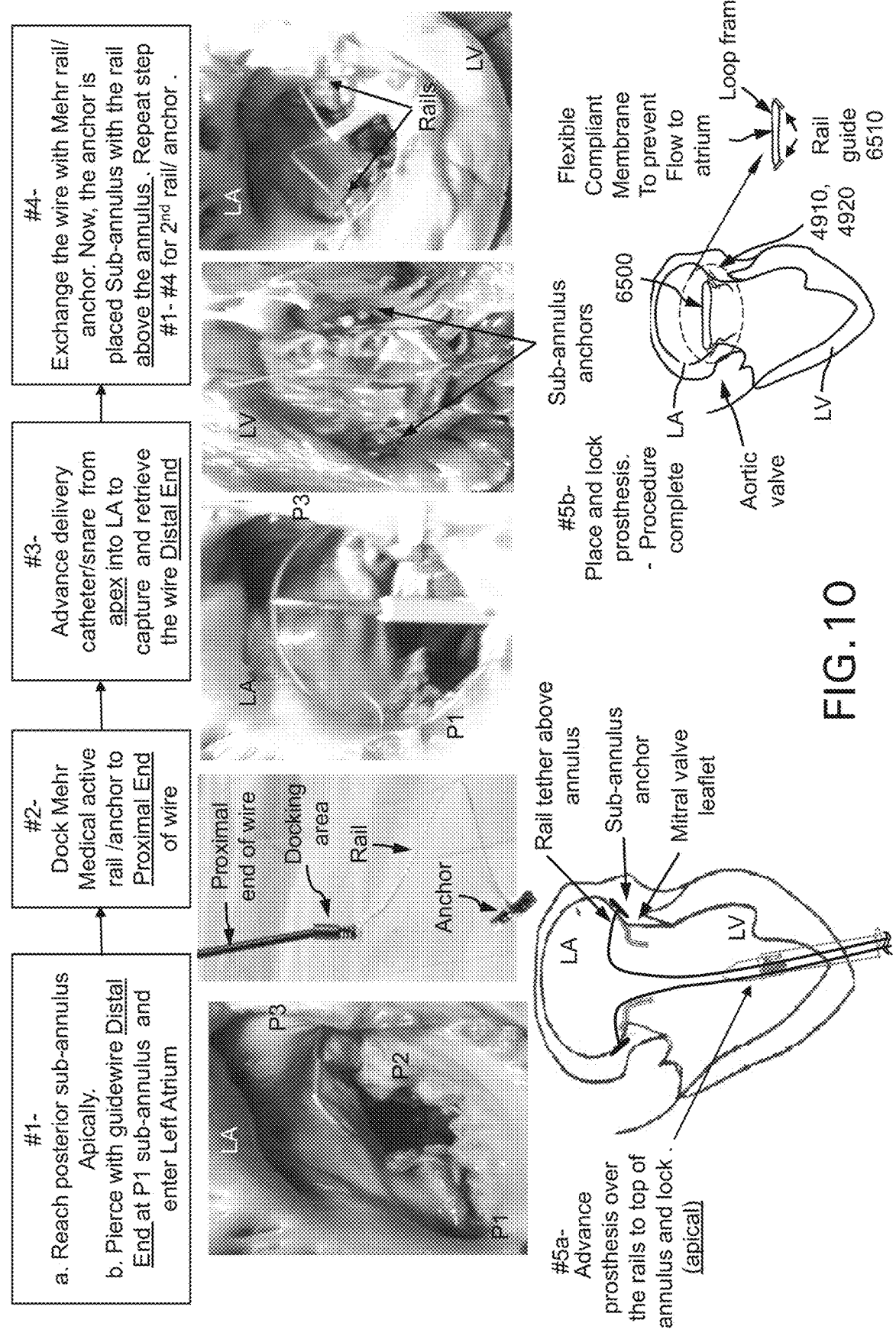
FIG. 10 illustrates an exemplary guide rail based prosthesis delivery technique using an apical approach through the left ventricle.

FIG. 9 illustrates a percutaneous approach using the devices illustrated herein. FIG. 10 describes an apical approach. The methods themselves are described in further detail in International Application No. PCT/US2011/59586, filed Nov. 7, 2011 which are incorporated by reference herein above.

All statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The methods and systems of the present disclosure, as described above and shown in the drawings, provide for improved techniques for treating mitral valves of patients. It will be apparent to those skilled in the art that various modifications and variations can be made in the devices, methods and systems of the present disclosure without departing from the spirit or scope of the disclosure. Thus, it is intended that the present disclosure include modifications and variations that are within the scope of the subject disclosure and equivalents.

What is claimed is:

1. A prosthesis delivery system, comprising:
   a) an elongate inner body having a proximal portion and a distal tip, the distal tip including a first proximally extending tubular member having a freely floating proximal end, the first proximally extending tubular member and elongate inner body cooperating to define a first substantially annular chamber;
   b) an elongate tubular outer body having a proximal portion and a distal end, the elongate tubular outer body being disposed about a proximal region of the elongate inner body, the elongate tubular outer body being axially displaceable with respect to the elongate inner body, the distal end of the elongate tubular outer body being configured to substantially abut the proximal end of the first proximally extending tubular member, a distal region of the elongate tubular outer body and the proximal region of the elongate inner body cooperating to define a second substantially annular chamber, the first and second chambers cooperating to define a prosthesis chamber for receiving a compressed prosthesis; and
   c) a compressed prosthesis disposed about the elongate inner body in the prosthesis chamber, the compressed prosthesis having at least one rail eyelet for receiving a flexible rail, the at least one rail eyelet extending radially outwardly through a juncture defined between the distal end of the elongate tubular outer body and the proximal end of the first proximally extending tubular member, the compressed prosthesis being configured to expand radially outwardly when the elongate inner body is advanced distally with respect to the elongate tubular outer body, and further wherein the elongate inner body and tubular outer body can be withdrawn proximally through a lumen defined by the prosthesis after deployment of the prosthesis without needing to disturb the prosthesis or anything in physical contact with the prosthesis.

2. The prosthesis delivery system of claim 1, further comprising a radiopaque marker mounted on the system proximate the prosthesis chamber.

3. The prosthesis delivery system of claim 2, wherein the radiopaque marker is mounted on the first proximally extending tubular member.

4. The prosthesis delivery system of claim 1, wherein the compressed prosthesis includes a plurality of rail eyelets, wherein each rail eyelet is configured to receive a flexible rail.

5. The prosthesis delivery system of claim 1, wherein the compressed prosthesis includes two rail eyelets, wherein each rail eyelet is configured to receive a flexible rail.

6. The prosthesis delivery system of claim 1, wherein the compressed prosthesis includes a generally tubular body adapted for placement proximate a mitral annulus, the tubular body having:
   a) a generally tubular upper portion adapted to substantially reside in the left atrium above the mitral annulus, the generally tubular upper portion having a first circumferential wall that is outwardly biased to urge against cardiac tissue of the left atrium, the first circumferential wall including a plurality of independently articulable frame portions configured to grip around the circumference of the atrial side of the mitral annulus;

b) a generally tubular lower portion extending downwardly from the generally tubular upper portion, the generally tubular lower portion being configured to substantially reside in the left ventricle below the mitral annulus, the lower portion being defined by an generally circumferential wall that extends downwardly from the generally tubular upper portion, the generally tubular lower portion including at least one independently articulable anchor biased to extend radially outwardly from the generally tubular lower portion to urge against the ventricular side of the mitral annulus to prevent the prosthesis from moving through the mitral opening toward the atrium; and c) at least one prosthetic valve leaflet disposed within the tubular body, the at least one prosthetic valve leaflet being configured to occupy at least a portion of an opening defined by the generally tubular upper portion and the lower portion.

7. The prosthesis delivery system of claim 6, wherein the prosthesis includes a plurality of independently articulable anchors biased to extend radially outwardly from the generally tubular lower portion to urge against the ventricular side of the mitral annulus to prevent the prosthesis from moving through the mitral opening toward the atrium.

8. The prosthesis delivery system of claim 6, wherein the prosthesis includes a fabric spanning across a framework of the prosthesis.

9. The prosthesis delivery system of claim 1, wherein the compressed prosthesis includes a generally tubular body adapted for placement proximate a mitral annulus, the tubular body having:

a) a generally tubular upper portion adapted to substantially reside in the left atrium above the mitral annulus, the generally tubular upper portion having a first circumferential wall that is outwardly biased to urge against cardiac tissue of the left atrium, the first circumferential wall including a plurality of independently articulable frame portions configured to grip around the circumference of the atrial side of the mitral annulus;

b) a generally tubular lower portion extending downwardly from the generally tubular upper portion, the generally tubular lower portion being configured to substantially reside in the left ventricle below the mitral annulus, the lower portion being defined by an generally circumferential wall that extends downwardly from the generally tubular upper portion, the generally tubular lower portion including at least one downwardly extending pole for permitting attachment of a tissue valve; and c) at least one prosthetic valve leaflet disposed within the tubular body, the at least one prosthetic valve leaflet being configured to occupy at least a portion of an opening defined by the generally tubular upper portion and the lower portion.

10. The prosthesis delivery system of claim 1, wherein the compressed prosthesis includes a generally tubular body adapted for placement proximate a mitral annulus, the tubular body having:

a) a generally tubular upper portion adapted to substantially reside in the left atrium above the mitral annulus, the generally tubular upper portion having a first circumferential wall having a first circumferential end and a second circumferential end, and defining a first circumferential gap therebetween, the generally tubular upper portion being biased to urge against cardiac tissue of the left atrium, the first circumferential wall including a plurality of independently articulable frame portions configured to grip around the circumference of the atrial side of the mitral annulus;

b) a generally tubular lower portion extending downwardly from the generally tubular upper portion, the generally tubular lower portion being configured to substantially reside in the left ventricle below the mitral annulus, the lower portion being defined by a generally circumferential wall that extends downwardly from the generally tubular upper portion and has a first circumferential end and a second circumferential end separated by a second circumferential gap therebetween; and c) at least one prosthetic valve leaflet disposed within the tubular body, the at least one prosthetic valve leaflet being configured to occupy at least a portion of an opening defined by the generally tubular upper portion and the lower portion.

11. The prosthesis delivery system of claim 1, wherein the prosthesis further includes an inflatable bladder disposed in the generally tubular lower portion of the prosthesis, the inflatable bladder being configured to be inflatable so as to facilitate adjustment of the prosthesis.

12. A system for delivering a prosthesis to a target location, comprising:

a) a tether delivery catheter for delivering an anchored tether to an anatomical location, including:

i) an elongate torqueable drive shaft having a proximal end with a first handle attached thereto and a distal end having a coupling for receiving an anchor;

ii) an anchor received in a torqueable relationship with the coupling of the distal end of the elongate torqueable drive shaft, the anchor having an anchoring portion to be advanced into an anatomical location, and at least one elongate tether extending proximally from the anchor toward the first handle; and iii) an outer tubular member having a proximal end, a distal end and an elongate body surrounding the elongate torqueable drive shaft, the outer tubular member including a handle proximate its proximal end, the second handle being rotatable with respect to the first handle about a central axis of the catheter to permit the anchor and elongate torqueable drive shaft to be rotated with respect to the outer tubular member; and b) a prosthesis delivery catheter, including:

i) an elongate inner body having a proximal portion and a distal tip, the distal tip including a first proximally extending tubular member having a freely floating proximal end, the first proximally extending tubular member and elongate inner body cooperating to define a first substantially annular chamber;

ii) an elongate tubular outer body having a proximal portion and a distal end, the elongate tubular outer body being disposed about a proximal region of the elongate inner body, the elongate tubular outer body being axially displaceable with respect to the elongate inner body, the distal end of the elongate tubular outer body being configured to substantially abut the proximal end of the first proximally extending tubular member, a distal region of the elongate tubular outer body and the proximal region of the elongate inner body cooperating to define a second substantially annular chamber, the first and second chambers cooperating to define a prosthesis chamber for receiving a compressed prosthesis; and iii) a compressed prosthesis disposed about the elongate inner body in the prosthesis chamber, the compressed prosthesis having at least one rail eyelet for receiving a flexible rail, the at least one rail eyelet extending radially outwardly through a juncture defined between the distal end of the elongate tubular outer body and the proximal end of the first proximally extending tubular member, the compressed prosthesis being configured to expand radially outwardly when the elongate inner body is advanced distally with respect to the elongate tubular outer body, and further wherein the elongate inner body and tubular outer body can be withdrawn proximally through a lumen defined by the prosthesis after deployment of the prosthesis without needing to disturb the prosthesis or anything in physical contact with the prosthesis.

* * * * *